(12) United States Patent
Futagawa et al.

(10) Patent No.: US 9,335,287 B2
(45) Date of Patent: May 10, 2016

(54) SPECIFICATION DEVICE FOR WATER STATUS OF SOIL, AND METHOD FOR SAME

(75) Inventors: Masato Futagawa, Toyohashi (JP);
Kazuaki Sawada, Toyohashi (JP)

(73) Assignee: National University Corporation Toyohashi University of Technology, Toyohashi-shi, Aichi (JP)

( * ) Notice: Subject to any disclaimer, the term of this patent is extended or adjusted under 35 U.S.C. 154(b) by 575 days.

(21) Appl. No.: 13/702,371

(22) PCT Filed: Jun. 14, 2011

(86) PCT No.: PCT/JP2011/063545
§ 371 (c)(1),
(2), (4) Date: Dec. 27, 2012

(87) PCT Pub. No.: WO2011/158812
PCT Pub. Date: Dec. 22, 2011

(65) Prior Publication Data
US 2013/0134994 A1 May 30, 2013

(30) Foreign Application Priority Data
Jun. 17, 2010 (JP) .................................. 2010-138443

(51) Int. Cl.
*G01N 27/04* (2006.01)
*G01N 33/24* (2006.01)

(52) U.S. Cl.
CPC ............ *G01N 27/048* (2013.01); *G01N 33/246* (2013.01)

(58) Field of Classification Search
CPC ............... G01N 27/333–27/401; G01N 27/36; G01N 27/302; G01N 27/048; G01N 33/246
See application file for complete search history.

(56) References Cited

U.S. PATENT DOCUMENTS

| | | | |
|---|---|---|---|
| 4,646,000 A * | 2/1987 | Wills | 324/674 |
| 2007/0273394 A1 | 11/2007 | Tanner et al. | |
| 2009/0095073 A1 | 4/2009 | Fukumura et al. | |
| 2011/0290649 A1 * | 12/2011 | Hamada et al. | 204/547 |

FOREIGN PATENT DOCUMENTS

| | | |
|---|---|---|
| JP | 2-103264 U | 8/1990 |
| JP | 09-506165 A | 6/1997 |
| JP | 2004-271494 A | 9/2004 |

(Continued)

OTHER PUBLICATIONS

International Search Report issued in corresponding PCT/JP2010/063545, dated Apr. 10, 2011.

(Continued)

*Primary Examiner* — Luan Van
*Assistant Examiner* — Gurpreet Kaur
(74) *Attorney, Agent, or Firm* — Yukiko O. Maekawa

(57) ABSTRACT

Contacting a pair of electrodes with soil, applying an alternate current input electric signal to one of the pair of electrodes, comparing a phase of an output electric signal from the other of the pair electrodes with a phase of the input electric signal; and determining the concentration of the ionic solute included in the solvent according to a difference of the phases. The difference of the phases is not dependent on the water content. An electrical conductivity is proportional to a water content and ion concentration, thereby, the water content of soil is available according to the measured electrical conductivity, while determining the ion concentration.

4 Claims, 12 Drawing Sheets

(56) References Cited

FOREIGN PATENT DOCUMENTS

| | | |
|---|---|---|
| JP | 2006-527356 A | 11/2006 |
| JP | 2008-14802 A | 1/2008 |
| JP | 2009-92633 A | 4/2009 |

OTHER PUBLICATIONS

English translation of International Preliminary Report on Patentability dated Jan. 15, 2013 issued in corresponding PCT application No. PCT/JP2011/063545, 6 pages.

* cited by examiner

PHASE CHANGE
TO WATER CONTENT

PHASE CHANGE
TO ION CONCENTRATION

EC OUTPUT CHANGE
TO WATER CONTENT

EC OUTPUT CHANGE
TO ION CONCENTRATION

ONE CONSTITUENT CIRCUIT REGARDED AS ONE PARASITIC ELEMENT

SPECIFICATION DEVICE FOR WATER STATUS OF SOIL, AND METHOD FOR SAME

TECHNICAL FIELD

The present invention relates to a determination device for a water status of soil and a method for determining a water status of soil.

BACKGROUND

A device for determining a status of soil is required for making agricultural work efficient and increasing productivity. As examples of water status specified, water content WC, electric conductivity EC, temperature, pH, and ion concentration are presented, for example.

As a water content sensor of prior art, for example, a tension meter, a TDR and a capacitance type sensor are known, as referred to the patent documents 1 and 2 below

RELATED PATENT DOCUMENT

Patent document 1: JP-A-2006-527356
Patent document 2: JP-A-H09-506165

SUMMARY OF THE INVENTION

Problems to be Solved by the Invention

To measure ion concentration of water included in soil presents an important barometer for understanding a nutrient status of the soil which cultivates agricultural crops.

Ion concentration in aqueous solution can be determined by electric conductivity $\sigma$ which is a reciprocal number of resistivity $\rho$. Such electric conductivity is obtained by measuring electric resistivity between a pair of electrodes which contact aqueous solution. However, in soil, all of the water constituents are not always formed into one continuous agglomerate of water. So, earth constituent, dirt and air included in soil, namely quantities left by eliminating water content from the soil per unit volume make effect on the measured electric conductivity of the soil. Namely, electric conductivity of water included in the soil, eventually ion concentration of water included in the soil cannot be determined exactly only by measuring resistance between electrodes which contact the soil.

Means for Solving the Problems

The inventors of the present invention have intensively studied to specify ion concentration of water included in soil.

The inventors noted the phase change of an electric signal applied to a pair of electrodes.

Then, the inventors found that such the phase change has a characteristic relation to the ion concentration included in the water regardless of the water content.

As described above, in the soil, all of the water droplets are not always formed into a continuous agglomerate of water. So, the electric conductivity of the water included in the soil, eventually the ion concentration of the water included in the soil cannot be determined exactly only by measuring resistance between electrodes which contact the soil.

In contrast, if the phase change is measured, the ion concentration included in the water can be determined regardless of the water content in the soil.

The lower surfaces of the pair of electrodes shown in FIG. 1 are made to contact the object to be measured. To the one electrode, an input electric signal of a predetermined frequency is applied. At the other electrode, an output electric signal is detected. On this occasion, the phase change $\theta$ is denoted by the following equation 1.

$$\theta = \tan^{-1} \frac{\text{Imaginary}}{\text{Real}} \quad \text{[Equation 1]}$$
$$= \tan^{-1} \frac{-\omega C R^2}{R}$$
$$= \tan^{-1}\left(-\omega \varepsilon \rho \frac{D}{WL} \frac{WL}{D}\right)$$
$$= \tan^{-1}(-\omega \varepsilon \rho)$$

Here, the characteristics of the aqueous solution are denoted as the following.

$$Z = \frac{1}{\frac{1}{R} + j\omega C} = \frac{R(1 - j\omega CR)}{1 + (\omega CR)^2} \quad \text{[Equation 2-1]}$$

$$R = \rho \frac{D}{WL} \quad \text{[Equation 2-2]}$$

$$C = \varepsilon \frac{WL}{D} \quad \text{[Equation 2-3]}$$

where Z is the impedance of the aqueous solution, R is the resistance between the electrodes in the aqueous solution, and C is the capacitance between the electrodes in the aqueous solution.

In the equation 1 described above, if the frequency value is fixed, $\omega$ and $\in$ become constant. As a result, the phase change $\theta$ is proportional to the arc tangent of the resistivity $\rho$. In other words, the phase change $\theta$ is proportional to the arc tangent of the reciprocal number of the electric conductivity $\sigma(=1/\rho)$. The electric conductivity $\sigma$ is proportional to the ion concentration of the aqueous solution. So, the phase change $\theta$ is proportional to the arc tangent of the reciprocal number of the ion concentration. In this case, the impedance Z has no effects.

More exactly, if the ion concentration changes, the dielectric constant $\in$ of the aqueous solution also changes. However, the change rate of the dielectric constant of the aqueous solution is very small as compared with the dielectric constant of water itself, the change rate of the dielectric constant can be neglected.

FIGS. 2A and 2B show the measured results of the phase change to the water content and the phase change to the ion concentration when the frequency is fixed.

The water content 1.0 shows the status of the aqueous solution. For example, the water content 0.4 shows that aqueous solution of 40 volume % is included in rock wool per unit volume As to FIGS. 2A and 2B, the phase changes are measured by a pair of aluminum electrodes with the size of 25 μm×4 mm which are positioned each other at the distance of 875 μm.

The measured diagrams of FIGS. 2A and 2B show that the phase change is not dependent on the water content but proportional only to the arc tangent of the reciprocal number of the ion concentration.

As described above, it is made clear that the ion concentration of the water included in the soil can be determined on a basis of the phase change $\theta$.

If soil is presumed to be material that dirt and air are dispersed in water, the disclosure above means that in a system dispersing another constituent B in solvent A, for example, water, the concentration of ionic solute can be determined by phase change. Here, the constituents B and A has the different electric conductive values respectively and the constituent B is not dissolved in the constituent A.

As the phase change is not dependent on water content, also the ion concentration of aqueous solution itself which does not include an insoluble constituent can be determined by the phase change.

The first aspect of the present invention is defined in the following.

A method for determining a concentration of ionic solute included in solvent of a dispersion system in which an ingredient insoluble in the solvent is dispersed in the solvent, comprising the steps of:

contacting a first pair of electrodes with the dispersion system;

applying an alternate current input electric signal to the one of the first pair of electrodes;

comparing a phase of an output electric signal from the other of the first pair electrodes with a phase of the input electric signal; and determining the concentration of the ionic solute included in the solvent according to a result of comparing the phases.

In the disclosure above, solvent is defined as material for dissolving solute without further limitative condition. In addition to water, petroleum solvent including alcohol, ether or the like may be used.

Solute dissolves in solvent and is presumed to be ionized to change the electric conductivity of the solvent in correspondence to the dissolution quantity.

An insoluble ingredient is presumed to be material which is insoluble to solvent and disperses in the solvent physically independent of the solvent, regardless of any kind of state, namely gas, liquid or solid. In addition, the insoluble ingredient is resumed to be material with high electric resistivity or insulating material. If the insoluble ingredient is conductive, the electric conductivity of the dispersion system is determined by the insoluble ingredient, so that the electric conductivity of the solvent cannot be obtained. It results in failure of getting the concentration of the solute in the solvent. Further, the relative dielectric constant of the solvent is presumed to be sufficiently larger than that of the insoluble ingredient. If the relative dielectric constant of the solvent is approximately equal to or smaller than the relative dielectric constant of the insoluble ingredient, the dielectric property is governed by the insoluble ingredient. As a result, in the measurement, the required concentration cannot be obtained by eliminating the effect of the water.

Inorganic material and organic material in solid state or air and gas like air may be used for the insoluble ingredient. If water is used for the solvent, oil may be used for the insoluble ingredient, and vice versa.

If soil is applied for the dispersion system, the solvent is constituted by water, and the solute is constituted by an ion of phosphor, potassium or the like, and the insoluble ingredient is constituted by solid constituents and air intervening between the solid constituents. The solid constituents are constituted by inorganic material including clay, the secondary particles related to the clay, or the like and organic material including the carcass of a creature or the like. In the present specification, the solid constituent is referred to an "earth constituent" and the air intervening between the solid constituents is referred to an "air constituent" hereinafter.

It is not necessarily required that the insoluble ingredient is dispersed uniformly in the dispersion system.

It is preferred that the chemically stable electrodes contact the dispersion system. For example, the electrodes may be formed of noble metal including gold, platinum, their alloy, or the like. In addition, the electrodes may be formed of carbon.

An input electric signal is inputted to the one of the electrodes, namely the first electrodes. The input electric signal is an alternate current signal. It is preferred that the frequency of the input electric signal is made constant when the concentration is measured.

Then, an output electric signal is measured at the other of electrodes, namely the second electrodes, to compare the phases of the input electric signal and the output electric signal. Concretely, as one mode for the comparison, the difference between the phases is measured.

In the soil, it is important to determine the water content.

FIGS. 3A and 3B show diagrams measured by a multipurpose electric conductivity sensor.

By referring to FIGS. 3A and 3B, it is recognized that the output of the electrical conductivity sensor (EC) is proportional to the water content and the ion concentration.

This is made clear from the following.

$$|Z| = \frac{R}{1+(\omega CR)^2}\sqrt{1+(\omega CR)^2} \quad \text{[Equation 3]}$$
$$= \frac{R}{\sqrt{1+(\omega CR)^2}}$$
$$= \rho\frac{D}{WL}\frac{1}{\sqrt{1+(\omega\varepsilon\rho)^2}}$$
$$= \frac{D}{WL}\frac{1}{\sqrt{\left(\frac{1}{\rho}\right)^2+(\omega\varepsilon)^2}}$$

Arc tangent of $1/\rho=\sigma$ (electric conductivity) is proportional to an ion concentration, and a dielectric constant $\in$ is proportional to a water content.

So, if the ion concentration is determined, the water content can be determined by the measured electric conductivity.

Accordingly, the ion concentration is determined by the phase change $\theta$, and the water content of the soil is determined by the measured electric conductivity on a basis of the determined ion concentration.

As described above, the water content is determined in the soil as an example of the dispersion system.

On a basis of the disclosure above, the fourth aspect of the present invention is defined in the following.

A method for determining a solvent volume in a dispersion system comprising the steps of:

measuring electric conductivity in the dispersion system; and determining the solvent quantity in the dispersion system on a basis of the electric conductivity measured and the concentration of the ionic solute determined by the method according to any of the first, the second and the third aspects of the present invention.

The fifth aspect of the present invention is proposed for a determination device for solvent quantity which practices the method for determining the solvent quantity.

A determination device for solvent volume comprising:
a semiconductor substrate;
a first pair of electrodes and a second pair of electrodes provided on the semiconductor substrate through an insulating layer;
a phase change determination unit connected with the first pair of electrodes for determining a phase change between the first pair of electrodes;
a phase change correction unit for correcting the phase change determined by the phase change determination unit on a basis of specific phase change determined on the semiconductor substrate;
an electric conductivity determination unit connected with the second pair of electrodes for determining electric conductivity between the second pair of electrodes; and
an electric conductivity correction unit for correcting the electric conductivity determined by the electric conductivity determination unit on a basis of specific electric conductivity determined on the substrate.

Inventors of the present invention have investigated another method for determining an ion concentration and a water content included in soil, as described in the following.

The water content is obtained by eliminating the earth constituent and the air constituent from the soil per unit volume. However, the water content in the soil includes a various kinds of ions including a potassium ion, a phosphor ion, or the like. So, when the water content is determined by processing the electric signal, an ion concentration in water cannot be neglected. It is note hereinafter that "ion concentration" is sometimes referred to "concentration".

It is recognized if the ion concentration included in the soil is identified, when the water content is determined, the effect of the ion concentration can be corrected. The ion concentration of the water can be determined by the electric conductivity. However, in the soil, all of the water constituents are not formed into one continuous volume of water. In other words, the earth volume and the air volume of the soil obtained by eliminating the water volume from the soil per unit volume have an effect on electric conductivity. So, the ion concentration of water cannot be determined exactly only by measuring the electric conductivity in the soil.

As described above, when the water content is determined, the electric conductivity has an effect on the water content. On the other hand, when the electric conductivity is determined, the water content has an effect on the electric conductivity. Accordingly, even if each characteristic is measured independently, each obtained value includes the error.

Inventors had intensively studied to solve such a problem. The Inventors found the problem relates to simultaneous equations concerning the water content and the electric conductivity. Namely, the Inventors found that the water content (apparent water content WC1) and the electric conductivity (apparent electric conductivity EC1) actually measured about the same soil can be processed simultaneously to infer the exact water content WC0 and the exact electric conductivity EC0.

As an index for measuring the water content, electrostatic capacitance value Q is used, since the electric conductivity has only a comparatively small effect on the electrostatic capacitance value Q. Here, in the present specification and claims, "electrostatic capacitance" is sometimes referred only to "capacitance".

The sixth aspect of the present invention is defined in the following.

A determination device for water status of soil comprising:
a semiconductor substrate;
a first pair of electrodes and a second pair of electrodes provided on the semiconductor substrate through an insulating layer;
an electric conductivity determination unit connected with the first pair of electrodes for determining electric conductivity between the first pair of electrodes; and
a capacitance determination unit connected with the second pair of electrodes for determining capacitance between the second pair of electrodes.

According to the determination device for water status of the sixth aspect of the present invention, as the first pair of electrodes for measuring the electric conductivity and the second pair of electrodes for measuring the electrostatic capacitance are provided on the same semiconductor substrate, the electric conductivity and the electrostatic capacitance Q can be measured for the soil on the same condition. Accordingly, the inferred values of the exact electric conductivity EC0 and the exact water content WC0 inferred from the process of the actually measured electric conductivity (apparent electric conductivity EC1) and electrostatic capacitance (apparent electrostatic capacitance Q1 corresponding to apparent water content WC1) secure high reliability.

The seventh aspect of the present invention is defined in the following. Namely, in the device according to the sixth aspect of the present invention, the second pair of electrodes is provided inside of the first pair of electrodes.

According to the determination device for water status of the seventh aspect of the present invention defined above, the first and the second electrodes may be positioned within a space as small as possible.

The arrangement of the first and the second pair of electrodes is not particularly limited if the first pair and the second pair of electrodes are positioned to measure common space on the substrate.

The constitution of the seventh aspect of the present invention is preferred for making the device more compact. On the other hand, the first pair of electrodes may be provided inside of the second pair of electrodes. In addition, the first pair and the second pair of electrodes may be provided alternately. Further, the first pair and the second pair of electrodes may be provided to cross the directions of the first pair and the second pair of electrodes each other.

The eighth aspect of the present invention is defined in the following. Namely, in the device according to the sixth aspect or the seventh aspect of the present invention, the first pair of electrodes and the second pair of electrodes are mutually isolated by an insulating layer of which surface is made hydrophilic.

As described above, since the surface of the insulating layer becomes hydrophilic, each pair of electrodes fit water included in the soil to extend the measurement range.

A way of processing the surface hydrophilic is not particularly limited. For example, on the surface of the insulating layer, the hydrophilic layer may be formed of a silicon oxide film or the like.

EMBODIMENTS

Figure 1:
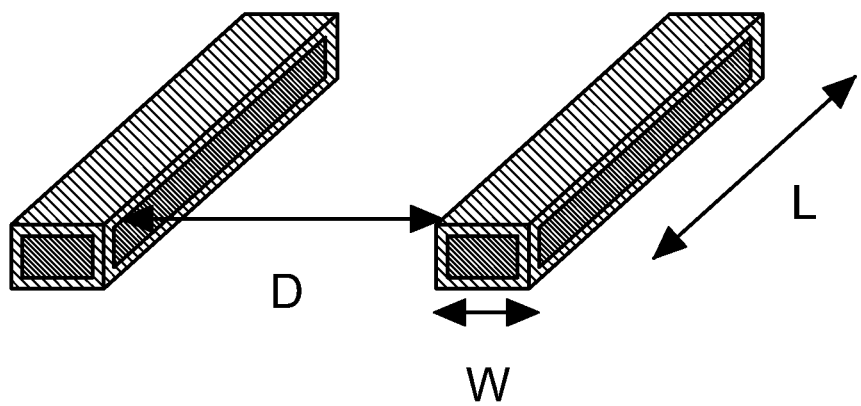
FIG. 1 is a conceptual diagram showing the structure of electrodes applied for the equation 1 on the phase change.
Figure 2A:
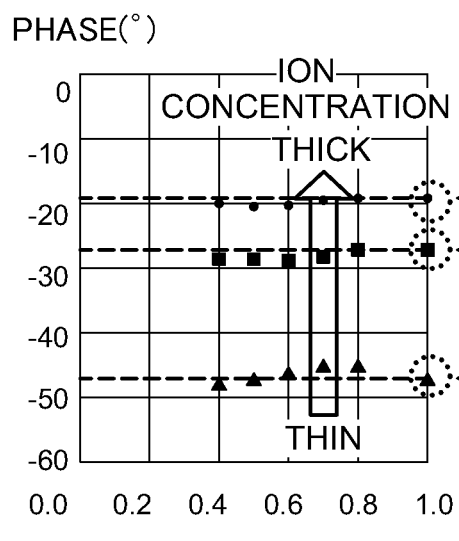
FIGS. 2A and 2B are diagrams showing the measured results of phase change to water content and phase change to ion concentration respectively when each frequency is fixed.
Figure 2B:
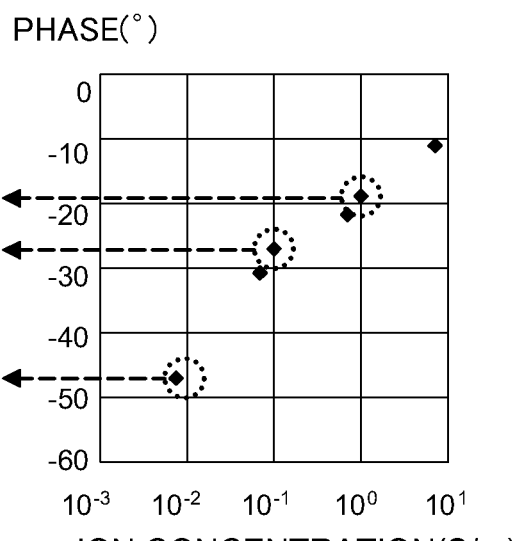
Figures 3A, 3B:
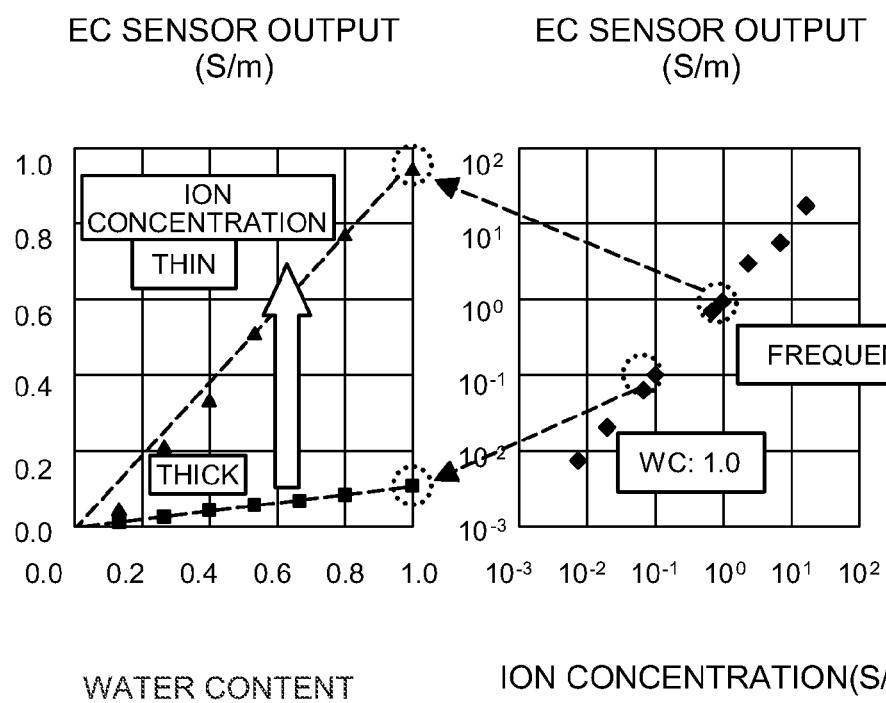
FIGS. 3A and 3B are diagrams showing the measured results of electric conductivity to water content and electric conductivity to ion concentration respectively when each frequency is fixed.
Figure 4:
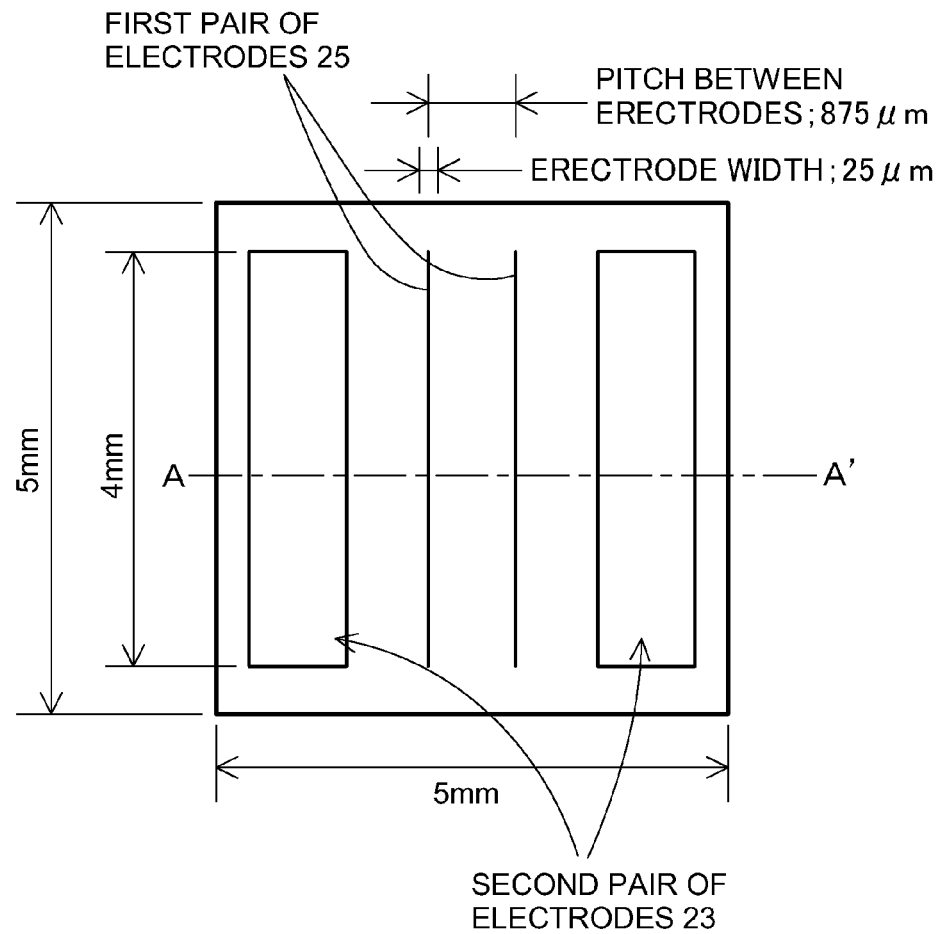
FIG. 4 is a plan view showing the constitution of a head unit.
Figure 5:
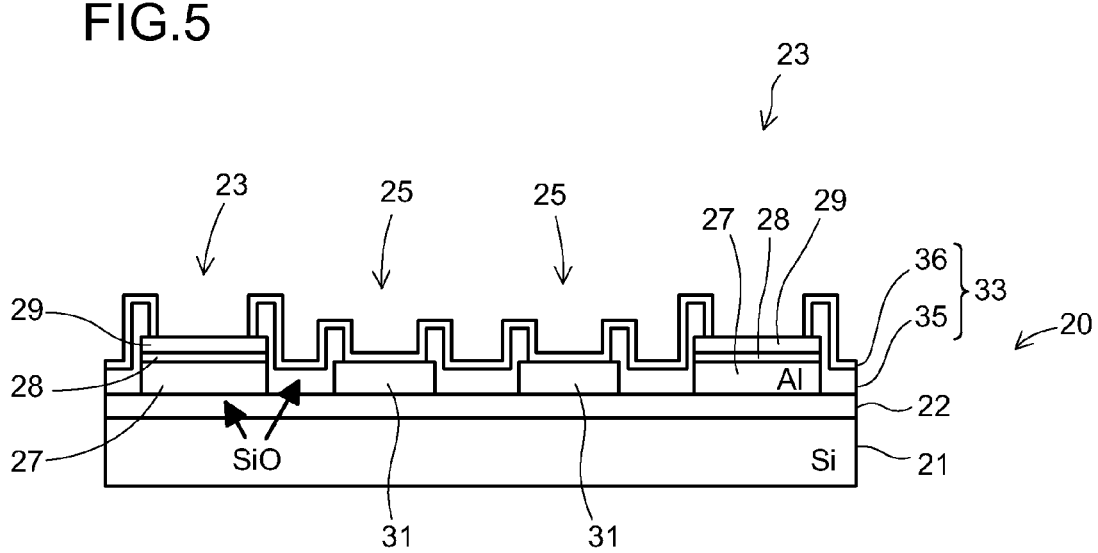
FIG. 5 is a sectional view showing the constitution of a head unit.

FIG. 4 is a plan view showing a head unit 20 of a sensor of an embodiment. FIG. 5 is a sectional view showing the constitution of the head unit 20.

As shown in FIG. 5, the head unit 20 is provided with a silicon substrate 21 and a silicon oxide insulating layer 22 which is 0.5 μm thick and formed by oxidizing the surface of the silicon substrate.

On the insulating layer 22, the first pair of electrodes 25 and the second pair of electrodes 23 are stacked.

As shown in FIG. 4, as to the second pair of electrodes 23, the width of each electrode is about 1 mm, the length of each electrode is about 4 mm, and the distance between the electrodes is about 2.5 mm.

In each of the second pair of electrodes 23, a platinum layer 29 with the layer thickness of 0.1 μm is stacked on the first layer 27 formed of aluminum with the layer thickness of 1 μm through a bonding layer 28 formed of titanium with the layer thickness of 0.02 μm.

The first pair of electrodes 25 are formed of the first layer 31 which is made of aluminum and 1 μm thick. The first layer 31 may be formed simultaneously with the first layer 27 of the second pair of electrodes 23. In the first pair of electrodes 25, the width of the first layer 31 is 25 μm, and the distance between the electrodes is 875 μm. In addition, in the first pair of electrodes 25, the relation W/D>100 is preferred wherein D denotes the film thickness of the upper protection film formed of a silicon nitride film, a silicon oxide film, or the like over each electrode and W denotes the distance between the electrodes. Such the relation results from the fact that the film thickness D relates to the capacitance of the upper protection film over electrodes 25 and the distance W relates to the capacitance of the space to be measured. In general, if W or D becomes smaller, each capacitance becomes larger. Here, the total capacitance in serial connection depends on the minimum capacitance value of the respective constituent capacitance values. For example, if a 100 pF capacitor and a 1 pF capacitor are serially connected, the total capacitance value becomes about 1 pF. Further, the relative dielectric constant of water is about hundred times larger than that of the protection film. Taking such the total capacitance in serial connection and the relative dielectric constant into consideration, it is dispensable to make the capacitance of the space to be measured smaller than that of the protection film.

Of course, a material of the metallic layer constituting these electrodes may be selected in accordance with its usage and object.

Each of the pairs of electrodes is isolated by the second insulating layer 33.

In this example, as the second insulating layer 33, a silicon oxide layer 35 with the layer thickness of 0.5 μm and a silicon nitride layer 36 with the layer thickness of 50 nm are stacked respectively on the substrate. In addition, the silicon nitride layer 36 also covers the surface of the first pair of electrodes 25. As the first pair of electrodes 25 is used to measure capacitance, its surface may be covered with the thin insulating film. Namely, the first layer 31 formed of aluminum is protected by the coverage of the insulating film. Further, the insulating film which covers the surface of the first pair of electrodes 25, is preferred more than or equal to $10^4 \times W \, \Omega m^2$, for reducing the effect of the electric conductivity of water on the capacitance value to be measured as much as possible.

Figure 6:
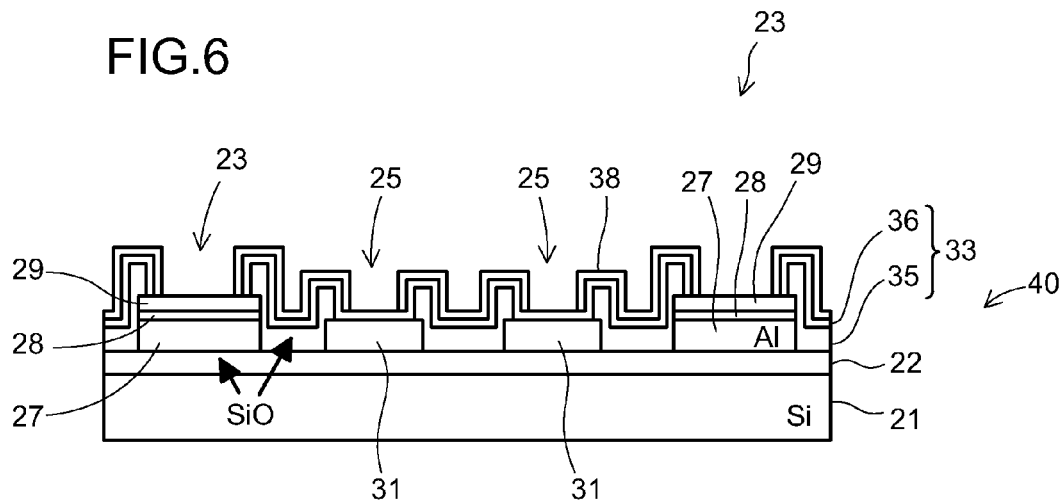
FIG. 6 is a sectional view showing the constitution of another head unit.

In a head unit 40 shown in FIG. 6, on the surface of the second insulating layer 35, a hydrophilic film 38 formed of a thin silicon oxide film with the film thickness of 60 nm is stacked to make the entire surface of the head unit 40 hydrophilic.

In this example, on the surface of the first pair of electrodes 25, the hydrophilic film 38 is not provided. However, for example, if the total thickness of the hydrophilic film 38 and the silicon nitride film 36 is less than or equal to 50 nm, the hydrophilic film 38 may be provided on the first pair of electrodes 25.

In addition, in the head unit 20 shown in FIG. 5 and the head unit 40 shown in FIG. 6, each layer may be formed by various methods. For example, the electrode layer may be formed with the patterning by sputtering method, and the second insulating layer 35 and the hydrophilic film 38 may be formed by CVD method.

Figure 7:
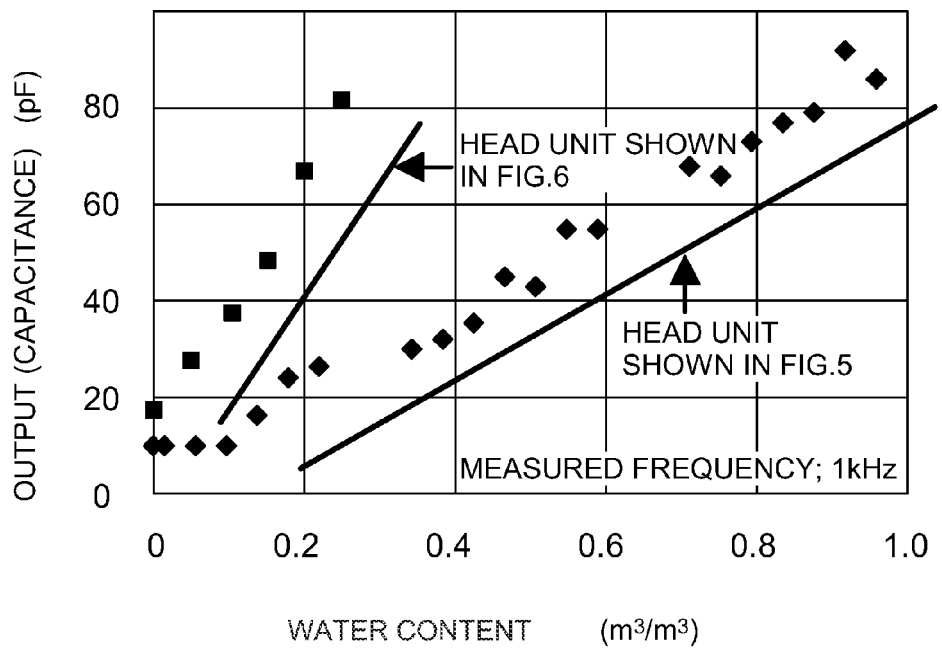
FIG. 7 is a diagram showing the relation between the water content of aqueous solution with constant ion concentration and the capacitance measured by a determination device for water status.

FIG. 7 shows the capacitance measured in the soil by the head unit 20 shown in FIG. 5 and the head unit 40 shown in FIG. 6. From the measured result shown in FIG. 7, it is read that the water content can be detected up to about 30%. From such the result, it is understood that the soil used for the measurement occupies about 70% of the space and the maximum water content contained in the space is 30%.

In this regard, according to the inventors' study, the head unit 20 with the hydrophobic surface shown in FIG. 5 is effective for the artificial soil including rock wool, for example. The measured range by the head unit 20 is wider than that by a type of head unit 40 shown in FIG. 6, because rock wool material occupies about 5%, namely a small ratio of the space and the water content can be contained up to 95%.

Figure 8:
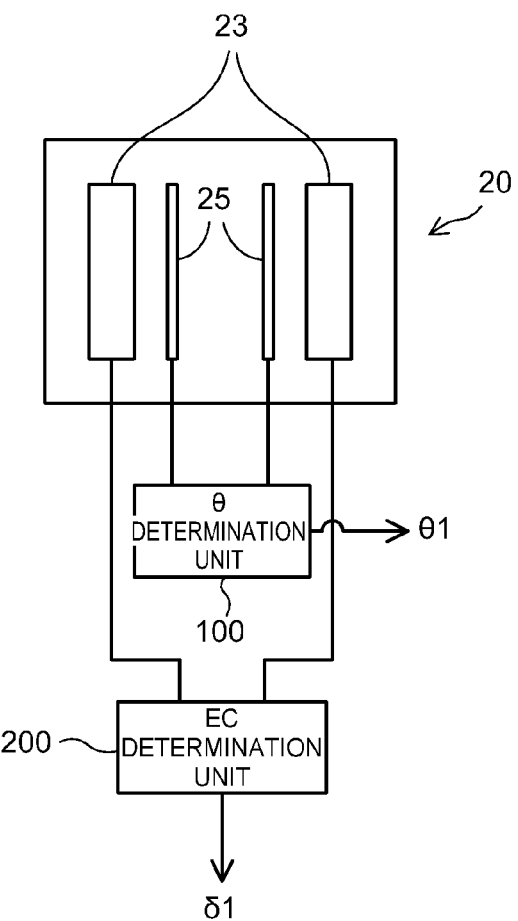
FIG. 8 is a conceptual diagram showing the constitution of a determination device for water status which is provided with the head unit 20 shown in FIG. 5.

A phase change determination unit 100 and an electric conductivity determination unit 200 as shown in FIG. 8 are connected to the head unit as shown in FIG. 5 provided with the respective electrodes 25, 23 which can realize wide detection range for the water content.

The phase change determination unit 100 applies to the one of the first electrodes 25 an AC electric signal with arbitrarily predetermined frequency to determine and output the phase change θ1, namely the phase difference between the phase of the AC signal applied to the one of the first pair of electrodes 25 and the phase of the output signal detected from the other of the first pair of electrodes.

The electric conductivity determination unit 200 determines the resistivity ρ between the second pair of electrodes 23 to get the electrical conductivity G1 from the resistivity ρ.

Figure 9A:
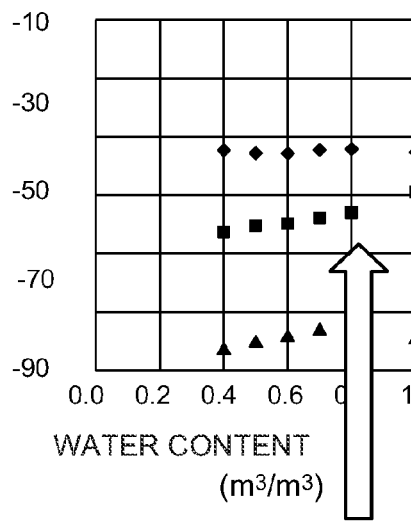
FIGS. 9A and 9B are diagrams showing output of a measuring device shown in FIG. 8.
Figure 9B:
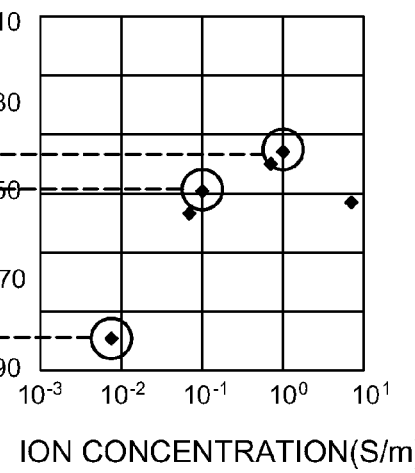

The object which had been measured to obtain the results of FIGS. 2A and 2B and FIGS. 3A and 3B was measured by the device shown in FIG. 8. As a result, the phase change θ1 and the electric conductivity σ shown in FIGS. 9A and 9B were obtained respectively. Namely, the device did not work according to a theory due to the intervening noises.

The cause of such the noises is understood as the following.

Namely, when the impedance of the object which relates to amplitude or phase for example is measured, the impedances of the interface oxide film and the substrate oxide film sometimes cause effects on the signal detected by the sensor.

In such a case, the correction is calculated as the following.

Figure 10A:
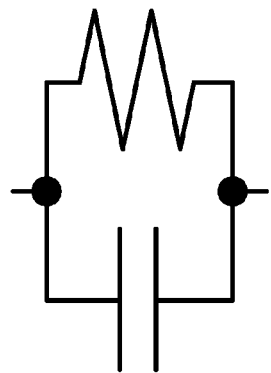
FIGS. 10A and 10B are diagrams for showing a correction principle in a measuring device.

First of all, since the phase change is detected in the dispersion system including the soil to be detected, the parallel circuit of the resistance R and the capacitance C is formed as an electric circuit in the dispersion system as shown in FIG. 10A.

An impedance Z of the parallel circuit is shown in the following.

$$Z = \frac{1}{\frac{1}{R} + j\omega C} \qquad [\text{Equation 4}]$$

Figure 10B:
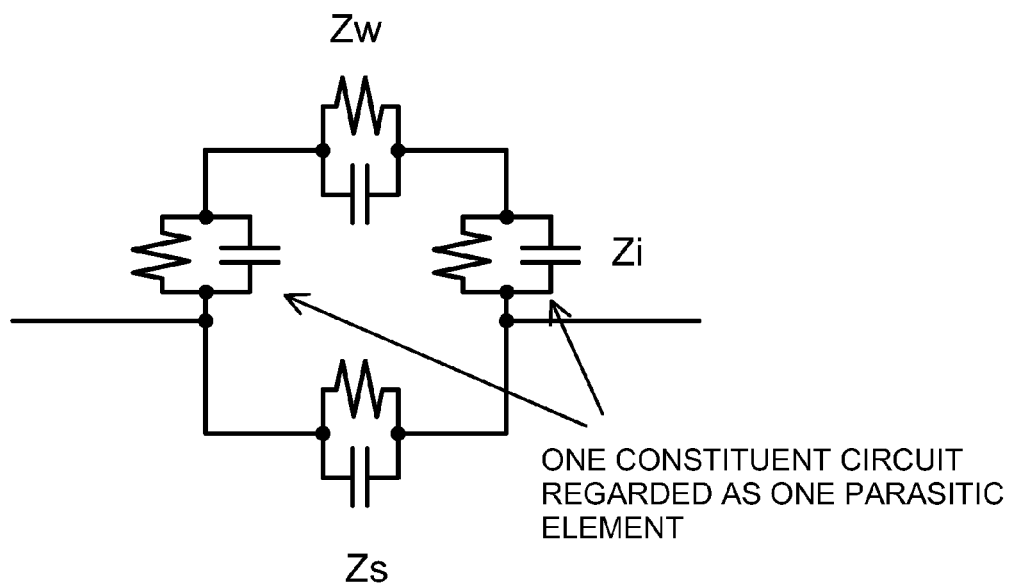

On the other hand, the first and the second electrodes 25, 23 are disposed on the semiconductor substrate, the resistance and the capacitance of the substrate itself have effects as shown in FIG. 10B. Further, it is necessary to consider the resistance and the capacitance between the substrate and the object to be measured.

The total impedance Zt of the circuit shown in FIG. 10B is expressed in the following.

$$Z_t = \frac{1}{\frac{1}{Z_s} + \frac{1}{Zw + Zi}} \qquad [\text{Equation 5}]$$

wherein Zs denotes the impedance of the substrate, Zw denotes the impedance of the measured object, and Zi denotes the impedance of the interface between the substrate and the measured object.

Zt can be measured directly by the sensor. If Zw is very large value, namely Zw is concerned only with air without contacting the object, the following equation can be obtained.

Zt=Zs

As described above, Zs can be obtained by actual measurement. Further, in condition of Zw<<Zi, namely when the sensor is immersed in a solution with sufficiently large ion concentration, the following equation can be obtained.

$$Z_t = \frac{1}{\frac{1}{Z_s} + \frac{1}{Z_i}} \qquad [\text{Equation 6}]$$

As Zt and Zs are known, Zi can be obtained by calculation. The equation above is converted into as the following.

$$Z_i = \frac{1}{\frac{1}{Z_t} - \frac{1}{Z_s}} \qquad [\text{Equation 7}]$$

In actual measurement, as the phase from phase θ is measured by the absolute value |Z| of impedance from the effective amplitude value, the following equation is obtained.

$$Z_i = \frac{1}{\frac{1}{|Z_t|(\cos\theta_t + j\sin\theta_t)} - \frac{1}{|Z_s|(\cos\theta_s + j\sin\theta_s)}} \qquad [\text{Equation 8}]$$

$$= \frac{1}{\frac{\cos\theta_t - j\sin\theta_t}{|Z_t|} - \frac{\cos\theta_s - j\sin\theta_s}{|Z_s|}} = |Z_i|e^{j\theta_i}$$

$$= \frac{1}{\frac{1}{|Z_t|}\cos\theta_t - \frac{1}{|Z_s|}\cos\theta_s - j\left(\frac{1}{|Z_t|}\cos\theta_t - \frac{1}{|Z_s|}\sin\theta_s\right)}$$

$$= \frac{\left(\frac{1}{|Z_t|}\cos\theta_t - \frac{1}{|Z_s|}\cos\theta_s\right) + j\left(\frac{1}{|Z_t|}\sin\theta_t - \frac{1}{|Z_s|}\sin\theta_s\right)}{\left(\frac{1}{|Z_t|}\cos\theta_t - \frac{1}{|Z_s|}\cos\theta_s\right)^2 + \left(\frac{1}{|Z_t|}\sin\theta_t - \frac{1}{|Z_s|}\sin\theta_s\right)^2}$$

$$= \frac{\left(\frac{1}{|Z_t|}\cos\theta_t - \frac{1}{|Z_s|}\cos\theta_s\right) + j\left(\frac{1}{|Z_t|}\sin\theta_t - \frac{1}{|Z_s|}\sin\theta_s\right)}{\frac{1}{|Z_t|^2} + \frac{1}{|Z_s|^2} - \frac{2(\cos\theta_t\cos\theta_s + \sin\theta_t\sin\theta_s)}{|Z_s||Z_t|}}$$

$$= \frac{\left(\frac{1}{|Z_t|}\cos\theta_i - \frac{1}{|Z_s|}\cos\theta_s\right) + j\left(\frac{1}{|Z_t|}\sin\theta_i - \frac{1}{|Z_s|}\sin\theta_s\right)}{\frac{1}{|Z_t|^2} + \frac{1}{|Z_s|^2} - \frac{2(\cos(\theta_t - \theta_s))}{|Z_s||Z_t|}}$$

Here, the following relation holds.

$$|Z| = \sqrt{(\text{REAL PART})^2 + (\text{IMAGINARY PART})^2}, \qquad [\text{Equation 9}]$$

$$\theta = \tan^{-1}\left(\frac{\text{IMAGINARY PART}}{\text{REAL PART}}\right)$$

So, the following equations are derived.

$$|Z_i| = \frac{\sqrt{\left(\frac{1}{|Z_t|}\sin\theta_t - \frac{1}{|Z_s|}\sin\theta_s\right)^2 + \left(\frac{1}{|Z_t|}\cos\theta_t - \frac{1}{|Z_s|}\cos\theta_s\right)^2}}{\frac{1}{|Z_t|^2} + \frac{1}{|Z_s|^2} - \frac{2(\cos(\theta_t - \theta_s))}{|Z_s||Z_t|}} \qquad [\text{Equation 10}]$$

$$\Theta_i = \tan^{-1}\left(\frac{\frac{1}{|Z_t|}\sin\theta_t - \frac{1}{|Z_s|}\sin\theta_s}{\frac{1}{|Z_t|}\cos\theta_t - \frac{1}{|Z_s|}\cos\theta_s}\right)$$

From the equations above, it is understood that the exact impedance value in the interface is calculated from the actual measurement.

Regardless of a kind of object to be measured, the interface value and the substrate value are constant. So, it is understood that the impedance values of the interface and the substrate can be obtained in advance to calculate the exact impedance value of the object to be measured in each case.

A method for calculating the impedance Zw of the space of which water content is not known is described in the following.

$$Zw = \frac{1}{\frac{1}{Zt} - \frac{1}{Zs}} - Zi \quad \text{[Equation 11]}$$

$$= \frac{1}{\frac{1}{|Z_t|e^{j\theta_t}} - \frac{1}{|Z_s|e^{j\theta_s}}} - |Z_i|e^{j\theta_i}$$

$$= \frac{1}{\frac{e^{-j\theta_t}}{|Z_t|} - \frac{e^{-j\theta_s}}{|Z_s|}} - |Z_i|e^{j\theta_i}$$

$$= \frac{1}{\frac{\cos\theta_t - j\sin\theta_t}{|Z_t|} - \frac{\cos\theta_s - j\sin\theta_s}{|Z_s|}} - |Z_i|e^{j\theta_i}$$

$$= \frac{1}{\frac{1}{|Z_t|}\cos\theta_t - \frac{1}{|Z_s|}\cos\theta_s - j\left(\frac{1}{|Z_t|}\sin\theta_t - \frac{1}{|Z_s|}\sin\theta_s\right)} - |Z_i|e^{j\theta_i}$$

$$= \frac{\left(\frac{1}{|Z_t|}\cos\theta_t - \frac{1}{|Z_s|}\cos\theta_s\right) + j\left(\frac{1}{|Z_t|}\sin\theta_t - \frac{1}{|Z_s|}\sin\theta_s\right)}{\left(\frac{1}{|Z_t|}\cos\theta_t - \frac{1}{|Z_s|}\cos\theta_s\right)^2 + \left(\frac{1}{|Z_t|}\sin\theta_t - \frac{1}{|Z_s|}\sin\theta_s\right)^2} - |Z_i|e^{j\theta_i}$$

$$= \frac{\left(\frac{1}{|Z_t|}\cos\theta_t - \frac{1}{|Z_s|}\cos\theta_s\right) + j\left(\frac{1}{|Z_t|}\sin\theta_t - \frac{1}{|Z_s|}\sin\theta_s\right)}{\frac{1}{|Z_t|^2} + \frac{1}{|Z_s|^2} - \frac{2(\cos\theta_t\cos\theta_s + \sin\theta_t\sin\theta_s)}{|Z_s||Z_t|}} - |Z_i|e^{j\theta_i}$$

$$= \frac{\left(\frac{1}{|Z_t|}\cos\theta_t - \frac{1}{|Z_s|}\cos\theta_s\right) + j\left(\frac{1}{|Z_t|}\sin\theta_t - \frac{1}{|Z_s|}\sin\theta_s\right)}{\frac{1}{|Z_t|^2} + \frac{1}{|Z_s|^2} - \frac{2(\cos(\theta_t - \theta_s))}{|Z_s||Z_t|}} - |Z_i|e^{j\theta_i}$$

$$= \frac{\left(\frac{1}{|Z_t|}\cos\theta_t - \frac{1}{|Z_s|}\cos\theta_s\right)}{\frac{1}{|Z_t|^2} + \frac{1}{|Z_s|^2} - \frac{2(\cos(\theta_t - \theta_s))}{|Z_s||Z_t|}} - |Z_i|\cos\theta_i +$$

$$j\left(\frac{\frac{1}{|Z_t|}\sin\theta_t - \frac{1}{|Z_s|}\sin\theta_s}{\frac{1}{|Z_t|^2} + \frac{1}{|Z_s|^2} - \frac{2(\cos(\theta_t - \theta_s))}{|Z_s||Z_t|}} - |Z_i|\sin\theta_i\right)$$

Here, the following equation holds. So, from the following equation, the following another equation can be obtained.

$$\theta = \tan^{-1}\left(\frac{\text{IMAGINARY PART}}{\text{REAL PART}}\right) \quad \text{[Equation 12]}$$

$$\theta_w = \tan^{-1}\left(\frac{\frac{\left(\frac{1}{|Z_t|}\sin\theta_t - \frac{1}{|Z_s|}\sin\theta_s\right)}{\frac{1}{|Z_t|^2} + \frac{1}{|Z_s|^2} - \frac{2(\cos(\theta_t - \theta_s))}{|Z_s||Z_t|}} - |Z_i|\sin\theta_i}{\frac{\left(\frac{1}{|Z_t|}\cos\theta_t - \frac{1}{|Z_t|}\cos\theta_s\right)}{\frac{1}{|Z_t|^2} + \frac{1}{|Z_s|^2} - \frac{2(\cos(\theta_t - \theta_s))}{|Z_s||Z_t|}} - |Z_i|\cos\theta_i}\right)$$

Even if the phase relation of the device becomes θt≠θ w by the effects of the interface and the substrate, the exact θw can be obtained according to the equations above by eliminating the effects of the interface and the substrate to calculate the ion concentration.

Similarly, the electric conductivity of the semiconductor substrate in itself and the electric conductivity in the interface between the semiconductor substrate and the measured object which are referred hereinafter as "specific electric conductivity σs" can be identified in advance.

Figure 11:
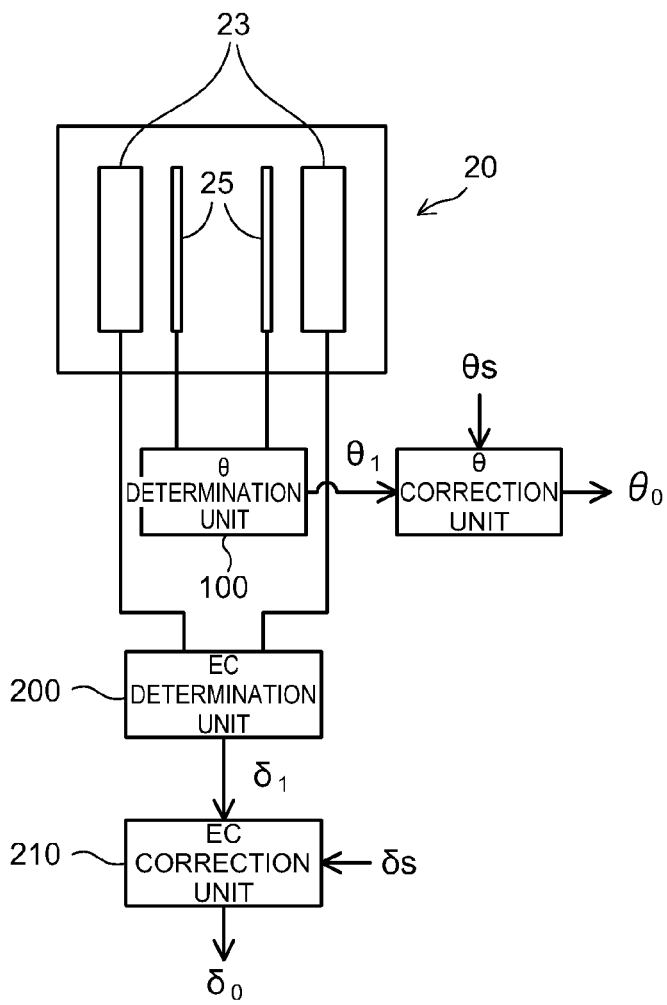
FIG. 11 is a conceptual diagram showing the constitution of a determination device for water status of an embodiment which is provided with a phase change correction unit and an electric conductivity correction unit.

Taking the descriptions above into consideration, in the device of FIG. 8, a phase change correction unit 110 for correcting the effect of the specific phase change θs from the actually measured phase change θ1 and an electrical conductivity correction unit 210 for correcting the effect of the specific electric conductivity σs from the actually measured electric conductivity σ1 are provided, as referred to FIG. 11.

FIGS. 2A and 2B and FIGS. 3A and 3B show the plotted result of the output θ0 of the phase change correction unit 110 and the output σs of the electric conductivity correction unit 210 in the apparatus shown in FIG. 11.

Here, the frequency of the input electric signal is 500 kHz, and the amplitude of the voltage is 250 mV. Standard ion solution is used. Insoluble ingredient is rock wool.

Figure 12:
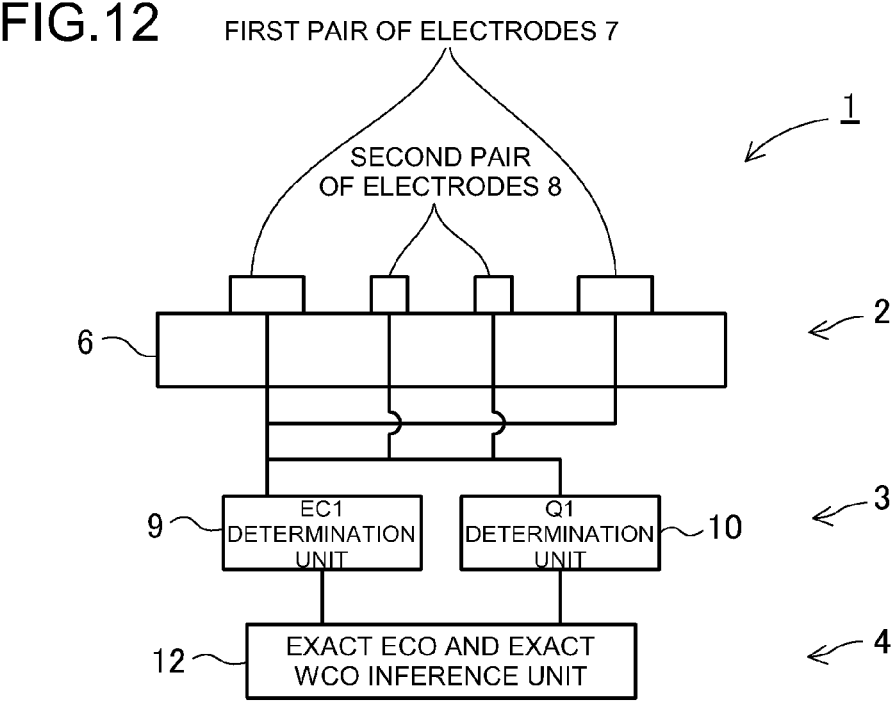
FIG. 12 is a block diagram showing the constitution of a determination device for water status of another embodiment.

FIG. 12 shows the constitution of a water content determination device 1 corresponding to the sixth aspect of the present invention.

The water content determination device 1 is provided with a head unit 2, a signal processing unit 3, and an inference unit 4.

The head unit 2 is provided with the first pair of electrodes 7 and the second pair of electrodes 8 on the surface of a semiconductor substrate 6 which is formed of silicon or the like. The head unit 2 is described below more in detail by referring to FIGS. 2 and 3.

The signal processing unit 3 is provided with an actually measured electric conductivity EC1 determination unit 9 and an actually measured capacitance Q1 determination unit 10. The EC1 determination unit 9 determines the electric conductivity of the soil on a basis the resistance between the first pair of electrodes 7. The obtained electric conductivity includes the effect of the water content, namely the air content and the earth constituent content of the soil. So, the obtained electric conductivity does not correspond to the exact ion concentration of the water included in the soil but the apparent electric conductivity EC1.

Similarly, the Q1 determination unit 10 determines the capacitance of the second pair of electrodes 8. In this example, the Q1 determination unit 10 utilizes an LCR indicator. The obtained capacitance includes the effect of the ion concentration of the water. So, the obtained capacitance does not correspond to the exact water content included in the soil but the apparent capacitance Q1.

An exact electric conductivity EC0 and exact water content WC0 inference unit 12 infers the exact electric conductivity EC0 and the exact water content WC0 from the actually measured values EC1 and Q1 which are determined by the EC1 determination unit 9 and the Q1 determination unit 10. The method for inferring is described below.

In this example, the head units shown in FIGS. 5 and 6 are used.

The method for inferring the exact electric conductivity EC0 and the exact water content WC0 on a basis of the actually measured electric conductivity EC1 determined by the EC1 determination unit 9 and the actually measured capacitance Q1 determined by the Q1 determination unit 10 is described in the following.

First of all, through the investigation, the inventors found the relation among the electrical conductivity, the capacitance, and the water content of the soil as described in the following.

Figure 13:
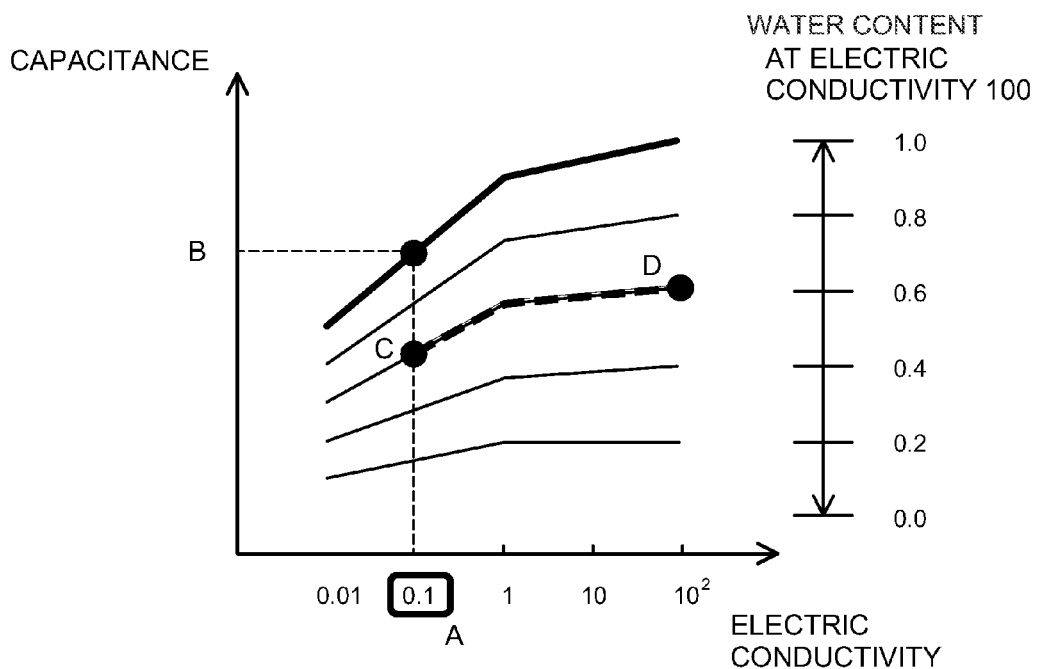
FIG. 13 is a diagram showing the relation between electric conductivity and capacitance.

FIG. 13 shows the relation between the electric conductivity and the capacitance. In FIG. 13, the relation between the electric conductivity and the capacitance in the aqueous solution of the water content 100% is shown by the thick line.

When each electric conductivity value is the same, the proportional relation is satisfied between the capacitance and the water content, as shown in FIG. 13. So, the relations between the electric conductivity and the capacitance in the water content values of 80%, 60%, 40% and 20% are shown by the thin lines in FIG. 13.

Figure 14:
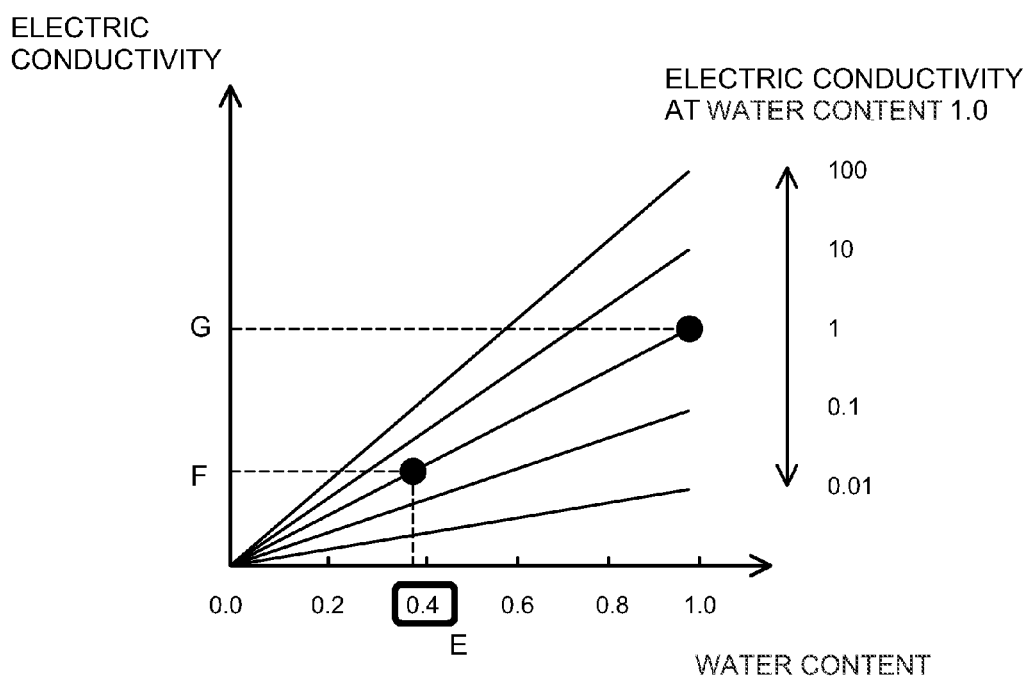
FIG. 14 is a diagram showing the relation between water content and electric conductivity.

FIG. 14 shows the relation between the water content and the electrical conductivity. As to the electrical conductivity in the water content 100%, if the water content becomes smaller, the electrical conductivity also becomes smaller in proportion to the water content.

Figure 16:
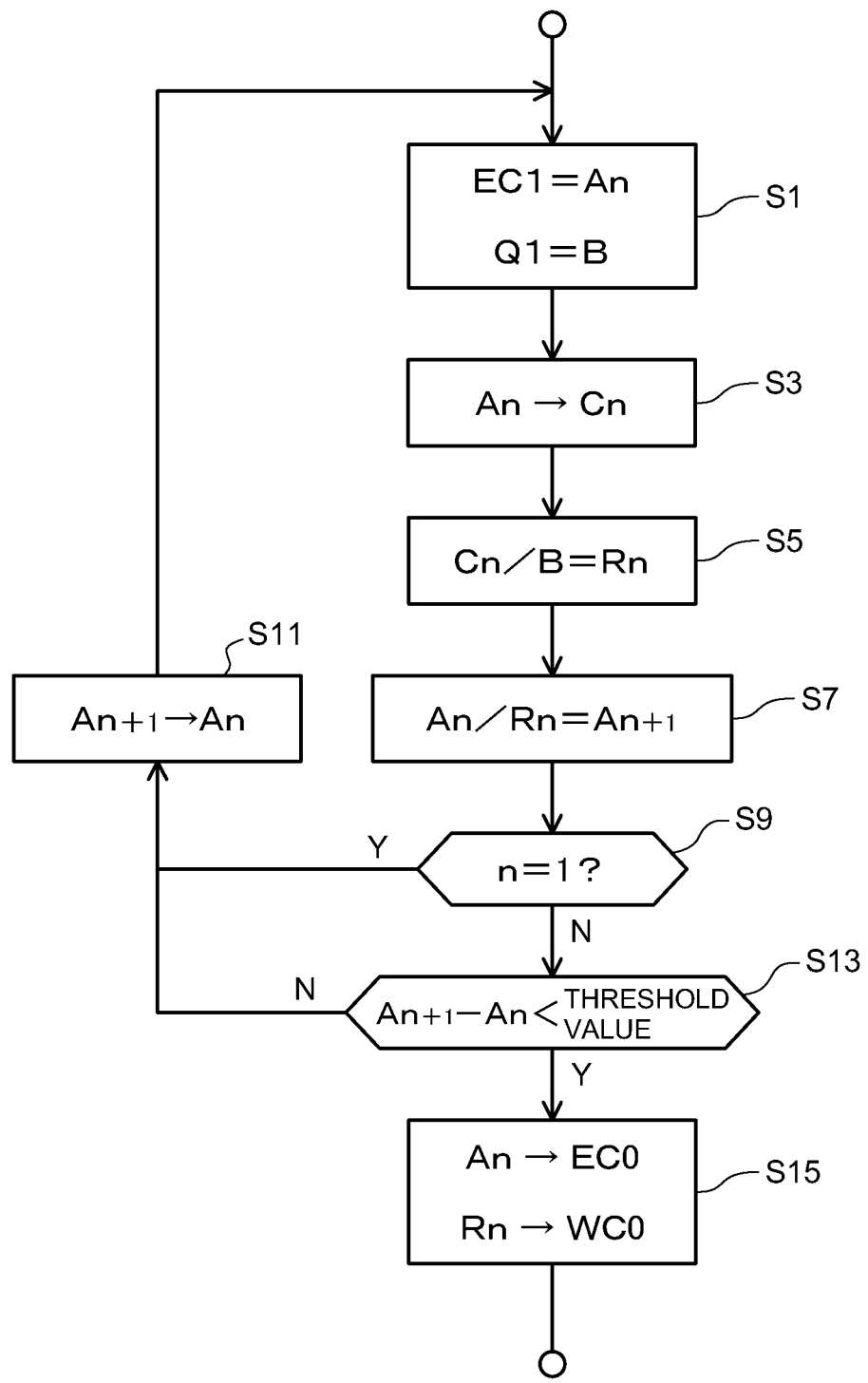
FIG. 16 is a diagram showing a flowchart for inferring exact values of water content and electric conductivity from actually measured values of water content and electric conductivity.

Under the precondition described above, it is assumed that in the measurement by the device shown in FIG. 12, the electrical conductivity EC1 (the first electric conductivity) becomes A1 and the capacitance Q1 (the first capacitance) becomes B, as referred to the step 1 in FIG. 16.

Figure 15:
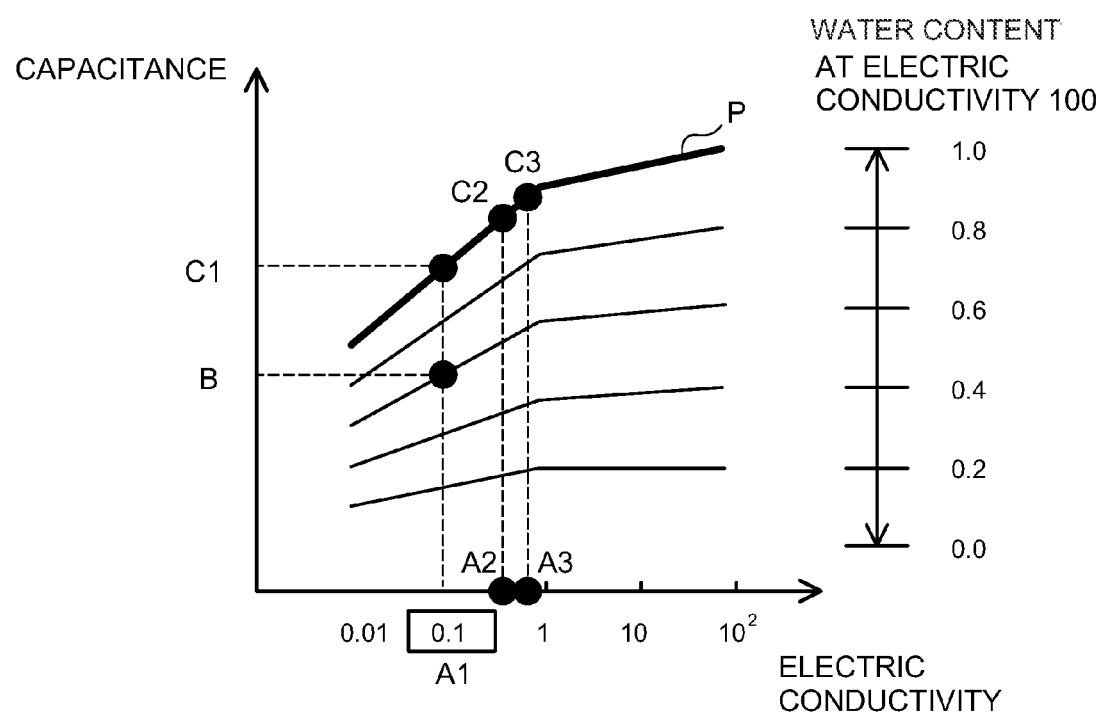
FIG. 15 is a diagram showing a method for inferring exact values of water content and electric conductivity from actually measured values of water content and electric conductivity.

The values A1 and B are plotted in the diagram of FIG. 13, as referred to FIG. 15.

As to the water of the same electric conductivity, namely the same ion concentration, the capacitance is proportional to the water content, as referred to FIG. 7. On the other hand, the relation of the thick line is obtained concerning the aqueous solution in advance. Here, the thick line shows the first relation between the electric conductivity and the capacitance. In accordance with such the relation of the thick line hereinafter referred to the first calibration line P, the capacitance C1 is obtained in correspondence to the electric conductivity A1, as referred to the step 3. Then, the ratio R1 of the actually measured capacitance B and the capacitance C1 is obtained, as referred to the step 5. As already described, the ratio R1 corresponds to the water content WC. For example, in the example shown in FIG. 15, as B/C is 0.6, the water content of the soil is presumed to be 0.6.

Next, as to the material of the same electric conductivity, the electric conductivity is proportional to the water content, as referred to FIG. 14. So, the actually measured electric conductivity A1 is divided by the ratio R1 corresponding to the water content WC, to determine the corrected electric conductivity A2, as referred to the step 7. Such the corrected electric conductivity A2 corresponds to the value of the electric conductivity obtained when the water content is presumed to be 100%.

Next, the steps 1-13 are repeated through the steps 9 and 11.

Namely, the capacitance C2 is determined on the calibration line P in correspondence to the corrected electric conductivity A2. Then, the ratio Rn of the capacitance C2 and the actually measured capacitance B is obtained. As the A2 is the electric conductivity obtained when the water content is presumed to be 100%, such the ratio Rn reflects the water content more exactly.

Further, the corrected electric conductivity A2 is divided by the obtained ratio Rn to determine the corrected electric conductivity A3. Next, the capacitance C3 is determined on the calibration line P in correspondence to the electric conductivity A3. Then, the ratio Rn of the capacitance C3 and the actually measured capacitance B is obtained. Such the ratio Rn reflects the water content more and more exactly.

Then, such the processes described above are repeated before the difference between the successively corrected An and An+1 becomes less than the predetermined threshold value, as referred to the step 13. In such the processes, when the electric conductivity An is obtained, the capacitance Cn is identified on the calibration line P in correspondence to the electric conductivity An. Next, the ratio Rn of the capacitance Cn and the actually measured B is obtained. The electric conductivity An and the ratio Rn become values respectively near to the exact electric conductivity EC0 of the water content and the exact water content WC0 included in the soil, as referred to the step 15.

In the example described above, the exact electric conductivity and the exact water content are inferred by correcting the electric conductivity on a basis of the actually measured capacitance. The reason why the capacitance is referred as the basis is described in the following. Namely, the abscissa axis corresponds to the change of the electric conductivity in a logarithmic scale, as shown in FIG. 13. In other words, the change of the capacitance is small as compared with the change of the electric conductivity.

On the other hand, the exact electric conductivity and the exact water content may also be inferred by correcting the capacitance on a basis of the actually measured electric conductivity.

The disclosure above is summarized in the following.

(1) A method for determining water status of soil comprising:
an electric conductivity measuring step of measuring electric conductivity of soil which is an object to be measured;
a capacitance measuring step of measuring capacitance of the soil;
a step of calculating a first electric conductivity measured by the electric conductivity measuring step and a first capacitance measured by the capacitance measuring step on a basis of a first relation between electric conductivity and capacitance determined on solution of different concentration in advance to obtain a ratio of capacitance determined on the first relation as to the electric conductivity and the first capacitance; and
a first electric conductivity determination step of correcting the first electric conductivity on a basis of the ratio to determine corrected electric conductivity.

(2) A method according to (1), further including a water content determination step of determining water content on a basis of ratio of the first capacitance and capacitance determined on the first relation as to the corrected electric conductivity.

(3) A method according to (1), further including a second electric conductivity determination step of calculating a ratio of capacitance determined on the first relation as to the corrected electric conductivity and the first capacitance, and further determining corrected electric conductivity on a basis of the ratio, wherein the method repeats the second electric conductivity determination step until a difference between electric conductivities before and after correction becomes less than a predetermined value.

(4) A method according to (3), further including a step of determining water content on a basis of a ratio of capacitance on the first relation and the first capacitance, the capacitance on the first relation being determined on the first relation as to the further corrected electric conductivity determined in the second electric conductivity determination step when a difference between the electric conductivities before and after correction becomes less than the predetermined value according to (3).

Another method for inferring is described hereinafter by referring to FIGS. 17 and 18. In FIG. 18, the same steps as those of FIG. 16 are referred to with the same reference numerals as those of FIG. 16 and the description thereof is eliminated.

As presupposition for another method for inferring, it is noted that in the relation between the electric conductivity and the capacitance, if the electric conductivity becomes more than the specific value which is $10^2 S/m^2$, for example, the capacitance changes little.

Figure 17:
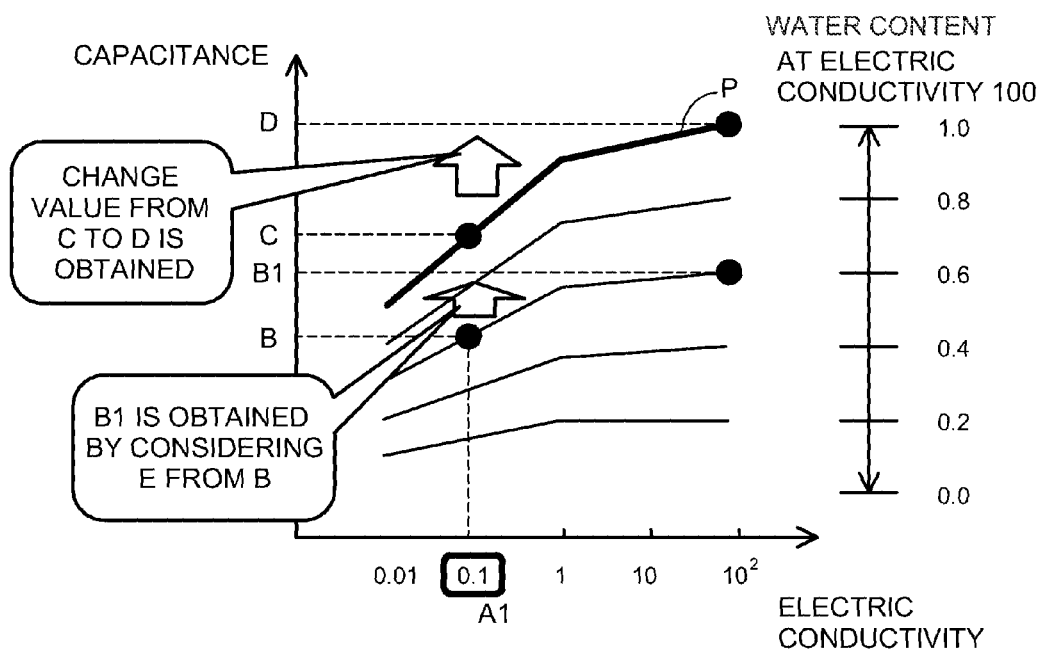
FIG. 17 is a diagram showing another method for inferring exact values of water content and electric conductivity from actually measured values of water content and electric conductivity.
Figure 18:
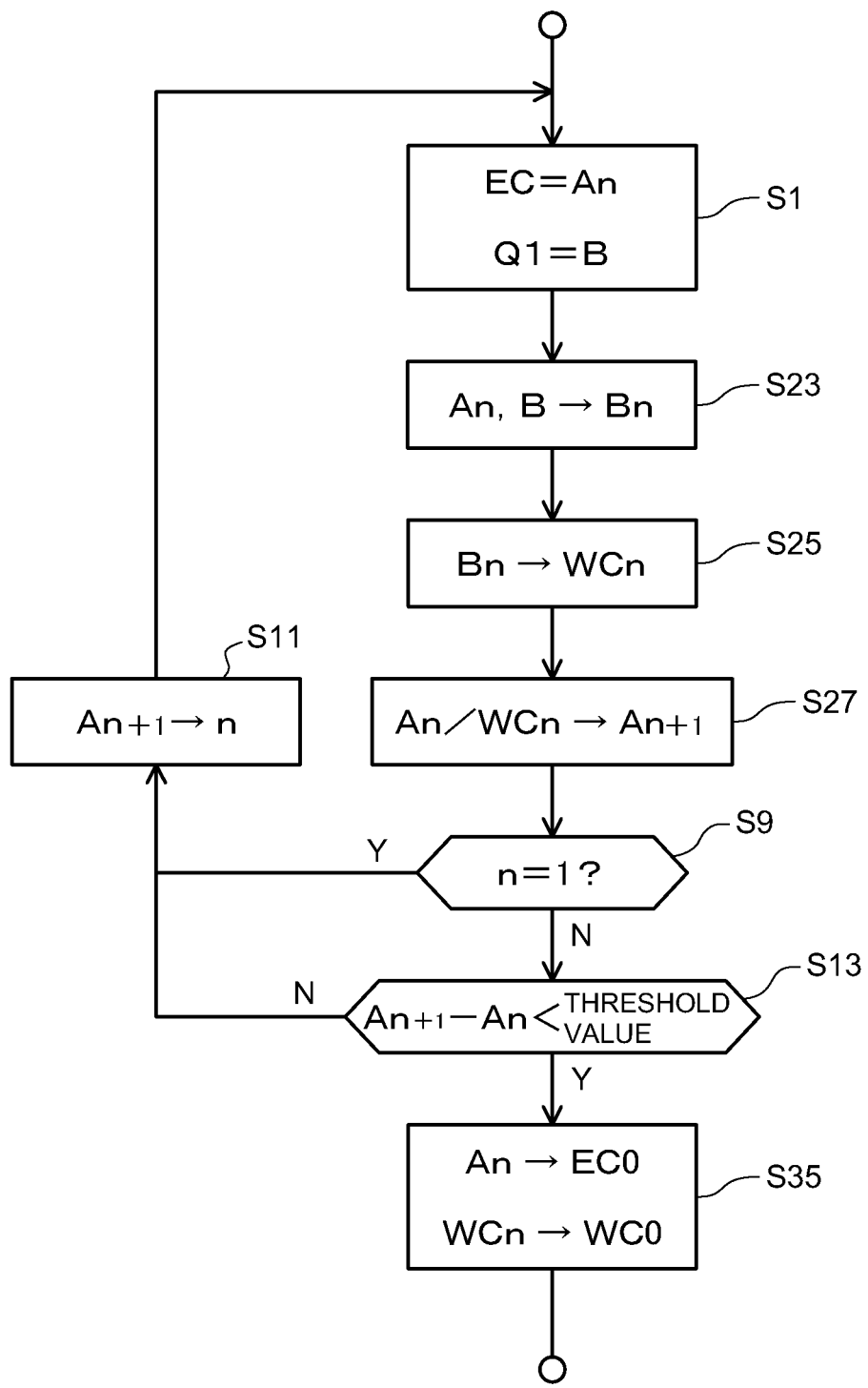
FIG. 18 is a diagram showing another flowchart for inferring exact values of water content and electric conductivity from actually measured values of water content and electric conductivity.

As shown in FIG. 17, the capacitance obtained in correspondence to the electric conductivity of $10^2 S/m^2$ is regarded as a basic value D. Then, as to the calibration line P, the ratio E of the capacitance and D is obtained and stored.

When the actually measured electric conductivity is A1 and the actually measure capacitance is B as referred to the step 1, the capacitance B1 is obtained by multiplying the capacitance B by the ratio E in correspondence to the actually measured electric conductivity A1, as referred to the step 23. The capacitance B1 is a capacitance value of the solution corresponding to the electric conductivity of $10^2 S/m^2$ which is used as a basis. Namely, when the electric conductivity of the water included in the soil is presumed to correspond to the basic value D, the capacitance B1 is obtained as the capacitance value of the soil.

As to the solutions with the same electric conductivity, the proportional relation is satisfied between the capacitance and the water content. So, if the calibration line between the capacitance and the water content is obtained in advance as to the solution with the electric conductivity of $10^2 S/m^2$ which is used as the basis as referred to FIG. 7, the water content WC1 can be determined correspondingly to the capacitance B1 according to the calibration line, as referred to the step 25.

The proportional relation is satisfied also between the water content and the electric conductivity. So, the actually measured electric conductivity A1 is corrected on a basis of the determined water content WC1. Concretely, the actually measured electric conductivity A1 is divided by the water content WC1, as referred to the step 27.

As to the corrected electric conductivity A2 obtained as described above, the capacitance B2 is obtained through multiplying the actually measured capacitance B by the ratio E corresponding to A2. Then, as described above, the water content WC2 is determined correspondingly to the capacitance B2. Further, the corrected electric conductivity A2 is modified on a basis of the water content WC2. Concretely, the modified electric conductivity A3 is obtained through by dividing the corrected electric conductivity A2 by the water content WC2.

The corrected electric conductivity An and the corrected water content WCn which are obtained by repeating the processes described above approach the respective exact values.

The processing method described above is represented as the following.

(10) A method for determining water status of soil comprising:

an electric conductivity measuring step of measuring electric conductivity of soil which is an object to be measured;

a capacitance measuring step of measuring capacitance of the soil;

a step of storing in advance a second relation between water content and capacitance as to solution with predetermined electric conductivity shown in FIG. 7;

a step of defining capacitance of the solution with predetermined electric conductivity as basic capacitance D, and storing ratio E of capacitance on calibration line P with changed electric conductivity and the basic capacitance D;

a step of determining water content WC1 in the solution with the predetermined electric conductivity on a basis of measured electric conductivity A1 and the ratio E; and a step of correcting the measured electric conductivity A1 on a basis of the water content WC1 which is determined, and determining corrected electric conductivity A2.

(11) A method for determining water status of soil according to (10) comprising:

a step of determining water content WC2 in the solution with the predetermined electric conductivity on a basis of the corrected electric conductivity A2 and the ratio E which are determined, wherein the method corrects the corrected electric conductivity again.

The present invention is not limited to the illustrated embodiments or examples alone, but may be changed and modified within the scope easily devised by those skilled in the art without departing from the spirit of the present invention.

In the embodiments described above, the electric conductivity and the capacitance of the soil are measured simultaneously by the head unit shown in FIG. 4. However, the electric conductivity and the capacitance of the soil may be measured by an electric conductivity sensor and a capacitance sensor constituted by respectively separated bodies.

An example of soil may be extended widely to a dispersion system for dispersing an insoluble ingredient in solvent which dissolves ionic solute.

DESCRIPTION OF THE REFERENCE NUMERALS

1 Determination device for water status of soil
2, 20, 40 Head unit
3, 21 Substrate
3 Signal processing unit
4 Inference unit
7, 25 First pair of electrodes
8, 23 Second pair of electrodes
100 Phase change determination unit
110 Phase change correction unit
200 Electric conductivity determination unit
210 Electric conductivity correction unit

The invention claimed is:

1. A method for determining a concentration of ionic solute included in a solvent of a dispersion system in which an ingredient that is insoluble in the solvent is dispersed in the solvent, wherein the solvent is at least 40 vol % of the dispersion system, comprising:
    contacting a first pair of electrodes with the dispersion system;
    applying an alternate current input electric signal to one electrode of the first pair of electrodes;
    comparing a phase of an output electric signal from the other electrode of the first pair electrodes with a phase of the input electric signal; and
    determining the concentration of the ionic solute included in the solvent according to a difference between the phase of the input electric signal and the phase of the output electric signal.

2. A method according to claim 1, wherein the solvent includes water, and the ingredient that is insoluble in the solvent includes air and an earth constituent.

3. A method for determining a solvent volume in the dispersion system comprising:
    measuring electric conductivity in the dispersion system; and
    determining a solvent quantity in the dispersion system on a basis of the electric conductivity measured and the concentration of the ionic solute determined by the method according to claim 1.

4. A method for specifying a concentration of ionic solute included in solvent of a dispersion system in which an ingredient that is insoluble in the solvent is dispersed in the solvent wherein the solvent is at least 40 vol % of the dispersion system, comprising:
    contacting a first pair of electrodes with the dispersion system;
    applying an alternate current input electric signal to one electrode of the first pair of electrodes;
    comparing a phase of an output electric signal from the other electrode of the first pair of electrodes with a phase of the input electric signal; and
    specifying the concentration of the ionic solute included in the solvent according to a difference between the phase of the input electric signal and the phase of the output electric signal.

* * * * *